United States Patent [19]

Clark et al.

[11] Patent Number: 4,879,227

[45] Date of Patent: Nov. 7, 1989

[54] PRODUCTION OF A RECOMBINANT HUMAN COLONY STIMULATING FACTOR

[75] Inventors: Steven C. Clark, Winchester; Gordon G. Wong, Cambridge, both of Mass.

[73] Assignee: Genetics Institute, Inc., Cambridge, Mass.

[21] Appl. No.: 860,377

[22] Filed: May 6, 1986

[51] Int. Cl.<sup>4</sup> ..................... C12P 21/02; C12N 15/00; C07H 15/12

[52] U.S. Cl. .................... 435/70; 435/172.3; 435/320; 536/27; 935/9; 935/11; 935/13

[58] Field of Search .................... 435/70, 172.3, 320; 935/9, 11, 13; 536/27

[56] References Cited

U.S. PATENT DOCUMENTS 4,438,032  3/1984  Golde et al. ..................... 435/172.2

FOREIGN PATENT DOCUMENTS 0261592  3/1988  European Pat. Off. .
0276551  8/1988  European Pat. Off. .

OTHER PUBLICATIONS

Manos, "Expression and Processing of a Recombinant Human Macrophage Colony-Stimulating Factor in Mouse Cells", *Molecular and Cellular Biology* 8(11): 5035-5039, Nov. 1988.

Rettenmier et al., "Differential Processing of Colony-Stimulating Factor 1 Precursors Encoded by Two Human cDNAs", *Molecular and Cellular Biology* 8(11); 5026-5034, Nov. 1988.

Ladner et al., "Human CSF-1: Gene Structure and Alternative Splicing of mRNA Precursors", *The EMBO JOurnal* 6(9): 2693-2698, 1987.

Wong et al., "Human CSF-1: Molecular Cloning and Expression of 4-kb cDNA Encoding the Human Urinary Protein", *Science* 235(4795): 1504-1508, 20 Mar. 1987.

Gough et al., Haematology and Blood Transfusion, vol. 29, pp. 380-384 (1985).

Wong et al., Science, vol. 228, pp. 810-815, May 17, 1985.

Wong et al., Cancer Cells 3, Growth Factors and Transformation, Cold Spring Harb. Lab., pp. 235-242 (1985).

Ralph, Leukocytes and Host Defense, 17th International Leukocytes Culture Conf., pp. 235-242, 1986.

Dunn et al., Cancer Cells 3, Growth Factors and Transformation, Cold Spring Harb. Lab., pp. 227-234 (1985).

Kawasaki et al., Science, vol. 230, pp. 291-296, Oct. 18, 1985.

Lusis et al., Nature, vol. 298, pp. 75-77, Jul. 1, 1982.

Gough et al., Nature, vol. 309, pp. 763-767, Jun. 28, 1984.

Gough et al., The EMBO J., vol. 4, pp. 645-653, Mar. 1985.

Hitzeman et al., Science, vol. 219, pp. 620-625, Feb. 11, 1983.

Kaufman et al., Mol. and Cell. Biol., vol. 2, pp. 1304-1319, Nov. 1982.

Miyatake et al., The EMBO J., vol. 4, pp. 2561-2568, 1985.

*Primary Examiner*—Alvin E. Tanenholtz
*Attorney, Agent, or Firm*—Bruce M. Eisen; David L. Berstein

[57] ABSTRACT

A process for producing a novel protein, CSF-69, is provided. The protein is capable of stimulating proliferation of monocytic lineage types cells in vitro assays. A novel DNA sequence codes on expression for CSF-69.

5 Claims, 2 Drawing Sheets

```
         10         20         30         40         50         60         70
CCTGGGTCCT CTCGGCGCCA GAGCCGCTCT CCGCATCCCA GGACAGCGGT GCGGCCCTCG GCCGGGCGC 80         90        100        110        120        130        140
CCACTCCGCA GCAGCCAGCG AGCGAGCGAG CGAGCGAGGG CGGCCGACGC GCCCGGCCGG GACCCAGCTG (-32)            160                 175                 190
CCCGT ATG ACC GCG CCG GGC GCC GCC GGG CGC TGC CCT CCC ACG ACA TGG CTG
      MET Thr Ala Pro Gly Ala Ala Gly Arg Cys Pro Pro Thr Thr Trp Leu 205                 220                 235               (1)
GGC TCC CTG CTG TTG TTG GTC TGT CTC CTG GCG AGC AGG AGT ATC ACC GAG GAG
Gly Ser Leu Leu Leu Leu Val Cys Leu Leu Ala Ser Arg Ser Ile Thr Glu Glu 250                 265                 280                 295
GTG TCG GAG TAC TGT AGC CAC ATG ATT GGG AGT GGA CAC CTG CAG TCT CTG CAG
Val Ser Glu Tyr Cys Ser His MET Ile Gly Ser Gly His Leu Gln Ser Leu Gln 310                 325                 340                 355
CGG CTG ATT GAC AGT CAG ATG GAG ACC TCG TGC CAA ATT ACA TTT GAG TTT GTA
Arg Leu Ile Asp Ser Gln MET Glu Thr Ser Cys Gln Ile Thr Phe Glu Phe Val 370                 385                 400
GAC CAG GAA CAG TTG AAA GAT CCA GTG TGC TAC CTT AAG AAG GCA TTT CTC CTG
Asp Gln Glu Gln Leu Lys Asp Pro Val Cys Tyr Leu Lys Lys Ala Phe Leu Leu 415                 430                 445                 460
GTA CAA GAC ATA ATG GAG GAC ACC ATG CGC TTC AGA GAT AAC ACC CCC AAT GCC
Val Gln Asp Ile MET Glu Asp Thr MET Arg Phe Arg Asp Asn Thr Pro Asn Ala 475                 490                 505
ATC GCC ATT GTG CAG CTG CAG GAA CTC TCT TTG AGG CTG AAG AGC TGC TTC ACC
Ile Ala Ile Val Gln Leu Gln Glu Leu Ser Leu Arg Leu Lys Ser Cys Phe Thr 520                 535                 550                 565
AAG GAT TAT GAA GAG CAT GAC AAG GCC TGC GTC CGA ACT TTC TAT GAG ACA CCT
Lys Asp Tyr Glu Glu His Asp Lys Ala Cys Val Arg Thr Phe Tyr Glu Thr Pro 580                 595            (122)610                 625
CTC CAG TTG CTG GAG AAG GTC AAG AAT GTC TTT AAT GAA ACA AAG AAT CTC CTT
Leu Gln Leu Leu Glu Lys Val Lys Asn Val Phe Asn Glu Thr Lys Asn Leu Leu 640                 655                 670
GAC AAG GAC TGG AAT ATT TTC AGC AAG AAC TGC AAC AAC AGC TTT GCT GAA TGC
Asp Lys Asp Trp Asn Ile Phe Ser Lys Asn Cys Asn Asn Ser Phe Ala Glu Cys 685                 700                 715                 730
TCC AGC CAA GAT GTG GTG ACC AAG CCT GAT TGC AAC TGC CTG TAC CCC AAA GCC
Ser Ser Gln Asp Val Val Thr Lys Pro Asp Cys Asn Cys Leu Tyr Pro Lys Ala
```

Figure 2 (Con't)

```
        745                    760                  775
ATC CCT AGC AGT GAC CCG GCC TCT GTC TCC CCT CAT CAG CCC CTC GCC CCC TCC
Ile Pro Ser Ser Asp Pro Ala Ser Val Ser Pro His Gln Pro Leu Ala Pro Ser 790              805(189)           820                 835
ATG GCC CCT GTG GCT GGC TTG ACC TGG GAG GAC TCT GAG GGA ACT GAG GGC AGC
MET Ala Pro Val Ala Gly Leu Thr Trp Glu Asp Ser Glu Gly Thr Glu Gly Ser 850                  865                  880                 895
TCC CTC TTG CCT GGT GAG CAG CCC CTG CAC ACA GTG GAT CCA GGC AGT GCC AAG
Ser Leu Leu Pro Gly Glu Gln Pro Leu His Thr Val Asp Pro Gly Ser Ala Lys 910                 925                 940
CAG CGG CCA CCC AGG AGC ACC TGC CAG AGC TTT GAG CCG CCA GAG ACC CCA GTT
Gln Arg Pro Pro Arg Ser Thr Cys Gln Ser Phe Glu Pro Pro Glu Thr Pro Val 955                  970                  985                 1000
GTC AAG GAC AGC ACC ATC GGT GGC TCA CCA CAG CCT CGC CCC TCT GTC GGG GCC
Val Lys Asp Ser Thr Ile Gly Gly Ser Pro Gln Pro Arg Pro Ser Val Gly Ala 1015                 1030                 1045
TTC AAC CCC GGG ATG GAG GAT ATT CTT GAC TCT GCA ATG GGC ACT AAT TGG GTC
Phe Asn Pro Gly MET Glu Asp Ile Leu Asp Ser Ala MET Gly Thr Asn Trp Val 1060                1075                 1090                 1105
CCA GAA GAA GCC TCT GGA GAG GCC AGT GAG ATT CCC GTA CCC CAA GGG ACA GAG
Pro Glu Glu Ala Ser Gly Glu Ala Ser Glu Ile Pro Val Pro Gln Gly Thr Glu 1120                 1135                 1150               1165
CTT TCC CCC TCC AGG CCA GGA GGG GGC AGC ATG CAG ACA GAG CCC GCC AGA CCC
Leu Ser Pro Ser Arg Pro Gly Gly Gly Ser MET Gln Thr Glu Pro Ala Arg Pro 1180                 1195                 1210
AGC AAC TTC CTC TCA GCA TCT TCT CCA CTC CCT GCA TCA GCA AAG GGC CAA CAG
Ser Asn Phe Leu Ser Ala Ser Ser Pro Leu Pro Ala Ser Ala Lys Gly Gln Gln 1225                 1240                 1255              1270
CCG GCA GAT GTA ACT GGT ACA GCC TTG CCC AGG GTG GGC CCC GTG AGG CCC ACT
Pro Ala Asp Val Thr Gly Thr Ala Leu Pro Arg Val Gly Pro Val Arg Pro Thr 1285                 1300                 1315
GGC CAG GAC TGG AAT CAC ACC CCC CAG AAG ACA GAC CAT CCA TCT GCC CTG CTC
Gly Gln Asp Trp Asn His Thr Pro Gln Lys Thr Asp His Pro Ser Ala Leu Leu 1330                 1345                 1360                  1375
AGA GAC CCC CCG GAG CCA GGC TCT CCC AGG ATC TCA TCA CTG CGC CCC CAG GGC
Arg Asp Pro Pro Glu Pro Gly Ser Pro Arg Ile Ser Ser Leu Arg Pro Gln Gly
```

Figure 2 (Con't)

```
        1390              1405             1420              1435
CTC AGC AAC CCC TCC ACC CTC TCT GCT CAG CCA CAG CTT TCC AGA AGC CAC TCC
Leu Ser Asn Pro Ser Thr Leu Ser Ala Gln Pro Gln Leu Ser Arg Ser His Ser 1450             1465              1480
TCG GGC AGC GTG CTG CCC CTT GGG GAG CTG GAG GGC AGG AGG AGC ACC AGG GAT
Ser Gly Ser Val Leu Pro Leu Gly Glu Leu Glu Gly Arg Arg Ser Thr Arg Asp 1495             1510              1525              1540
CGG AGG AGC CCC GCA GAG CCA GAA GGA GGA CCA GCA AGT GAA GGG GCA GCC AGG
Arg Arg Ser Pro Ala Glu Pro Glu Gly Gly Pro Ala Ser Glu Gly Ala Ala Arg 1555              1570             1585
CCC CTG CCC CGT TTT AAC TCC GTT CCT TTG ACT GAC ACA GGC CAT GAG AGG CAG
Pro Leu Pro Arg Phe Asn Ser Val Pro Leu Thr Asp Thr Gly His Glu Arg Gln 1600              1615             1630              1645
TCC GAG GGA TCC TCC AGC CCG CAG CTC CAG GAG TCT GTC TTC CAC CTG CTG GTG
Ser Glu Gly Ser Ser Ser Pro Gln Leu Gln Glu Ser Val Phe His Leu Leu Val 1660             1675             1690              1705
CCC AGT GTC ATC CTG GTC TTG CTG GCT GTC GGA GGC CTC TTG TTC TAC AGG TGG
Pro Ser Val Ile Leu Val Leu Leu Ala Val Gly Gly Leu Leu Phe Tyr Arg Trp 1720              1735              1750
AGG CGG CGG AGC CAT CAA GAG CCT CAG AGA GCG GAT TCT CCC TTG GAG CAA CCA
Arg Arg Arg Ser His Gln Glu Pro Gln Arg Ala Asp Ser Pro Leu Glu Gln Pro 1765            1780              1795                        1817
GAG GGC AGC CCC CTG ACT CAG GAT GAC AGA CAG GTG GAA CTG CCA GTG TAGAGGGAAT
Glu Gly Ser Pro Leu Thr Gln Asp Asp Arg Gln Val Glu Leu Pro Val 1827       1837       1847       1857       1867       1877       1887
TCTAAGCTGG ACGCACAGAA CAGTCTCTCC GTGGGAGGAG ACATTATGGG GCGTCCACCA CCACCCCTCC 1897       1907       1917       1927       1937       1947       1957
CTGGCCATCC TCCTGGAATG TGGTCTGCCC TCCACCAGAG CTCCTGCCTG CCAGGACTGG ACCAGAGCAG 1967       1977       1987       1997       2007       2017       2027
CCAGGCTGGG GCCCCTCTGT CTCAACCCGC AGACCCTTGA CTGAATGAGA GAGGCCAGAG GATGCTCCCC 2037       2047       2057       2067       2077       2087       2097
ATGCTGCCAC TATTTATTGT GAGCCCTGGA GGCTCCCATG TGCTTGAGGA AGGCTGGTGA GCCCGGCTCA 2107       2117       2127       2137       2147       2157       2167
GGACCCTCTT CCCTCAGGGG CTGCACCCTC CTCTCACTCC CTTCCATGCC GGAACCCAGG CCAGGGACCC
```

Figure 2 (Con't)

```
         2177       2187       2197       2207       2217       2227       2237
    ACCGGCCTGT GGTTTGTGGG AAAGCAGGGT GGACGCTGAG GAGTGAAAGA ACCCTGCACC CAGAGGGCCT 2247       2257       2267       2277       2287       2297       2307
    GCCTGGTGCC AAGGTATCCC AGCCTGGACA GGCATGGACC TGTCTCCAGA GAGAGGAGCC TGAAGTTCGT 2317       2327       2337       2347       2357       2367       2377
    GGGGCGGGAC AGCGTCGGCC TGATTTCCCG TAAAGGTGTG CAGCCTGAGA GACGGGAAGA GGAGGCCTCT 2387       2397       2407       2417       2427       2437       2447
    GGACCTGCTG GTCTGCACTG ACAGCCTGAA GGGTCTACAC CCTCGGCTCA CCTAAGTGCC CTGTGCTGGT 2457       2467       2477       2487       2497       2507       2517
    TGCCAGGCGC AGAGGGAGG CCAGCCCTGC CCTCAGGACC TGCCTGACCT GCCAGTGATG CCAAGAGGGG 2527       2537       2547       2557       2567       2577       2587
    GATCAAGCAC TGGCCTCTGC CCCTCCTCCT TCCAGCACCT GCCAGAGCTT CTCCAGGAGG CCAAGCAGAG 2597       2607       2617       2627       2637       2647       2657
    GCTCCCCTCA TGAAGGAAGC CATTGCACTG TGAACACTGT ACCTGCCTGC TGAACAGCCT GCCCCGTCC 2667       2677       2687       2697       2707       2717       2727
    ATCCATGAGC CAGCATCCGT CGGTCCTCCA CTCTCCAGCC TCTCCCAGC CTCCTGCACT GAGCTGGCCT 2737       2747       2757       2767       2777       2787       2797
    CACCAGTCGA CTGAGGGAGC CCCTCAGCCC TGACCTTCTC CTGACCTGGC CTTTGACTCC CCGGAGTGGA 2807       2817       2827       2837       2847       2857       2867
    GTGGGGTGGG AGAACCTCCT GGGCCGCCAG CCAGAGCCGG TCTTTAGGCT GTGTTGTTCG CCCAGGTTTC 2877       2887       2897       2907       2917       2927       2937
    TGCATCTTGC ACTTTGACAT TCCCAAGAGG GAAGGGACTA GTGGGAGAGA GCAAGGGAGG GGAGGGCACA 2947       2957       2967       2977       2987       2997       3007
    GACAGAGAGG CTACAGGGCG AGCTCTGACT GAAGATGGGC CTTTGAAATA TAGGTATGCA CCTGAGGTTG 3017       3027       3037       3047       3057       3067       3077
    GGGGAGGGTC TGCACTCCCA AACCCCAGCG CAGTGTCCTT TCCCTGCTGC CGACAGGAAC CTGGGGCTGA
```

Figure 2 (Con't)

```
      3087       3097       3107       3117       3127       3137       3147
GCAGGTTATC CCTGTCAGGA GCCCTGGACT GGGCTGCATC TCAGCCCCAC CTGCATGGTA TCCAGCTCCC 3157       3167       3177       3187       3197       3207       3217
ATCCACTTCT CACCCTTCTT TCCTCCTGAC CTTGGTCAGC AGTGATGACC TCCAACTCTC ACCCACCCCC 3227       3237       3247       3257       3267       3277       3287
TCTACCATCA CCTCTAACCA GGCAAGCCAG GGTGGGAGAG CAATCAGGAG AGCCAGGCCT CAGCTTCCAA 3297       3307       3317       3327       3337       3347       3357
TGCCTGGAGG GCCTCCACTT TGTGGCCAGC CTGTGGTGGT GGCTCTGAGG CCTAGGCAAC GAGCGACAGG 3367       3377       3387       3397       3407       3417       3427
GCTGCCAGTT GCCCCTGGGT TCCTTTGTGC TGCTGTGTGC CTCCTCTCCT GCCGCCCTTT GTCCTCCGCT 3437       3447       3457       3467       3477       3487       3497
AAGAGACCCT GCCCTACCTG GCCGCTGGGC CCCGTGACTT TCCCTTCCTG CCCAGGAAAG TGAGGGTCGG 3507       3517       3527       3537       3547       3557       3567
CTGGCCCCAC CTTCCCTGTC CTGATGCCGA CAGCTTAGGG AAGGGCAGTG AACTTGCATA TGGGGCTTAG 3577       3587       3597       3607       3617       3627       3637
CCTTCTAGTC ACAGCCTCTA TATTTGATGC TAGAAAACAC ATATTTTTAA ATGGAAGAAA AATAAAAAGG 3647       3657       3667       3677       3687       3697       3707
CATTCCCCCT TCATCCCCCT ACCTTAAACA TATAATATTT TAAAGGTCAA AAAAGCAATC CAACCCACTG 3717       3727       3737       3747       3757       3767       3777
CAGAAGCTCT TTTTGAGCAC TTGGTGGCAT CAGAGCAGGA GGAGCCCCAG AGCCACCTCT GGTGTCCCCC 3787       3797       3807       3817       3827       3837       3847
CAGGCTACCT GCTCAGGAAC CCCTTCTGTT CTCTGAGAAG TCAAGAGAGG ACATTGGCTC ACGCACTGTG 3857       3867       3877       3887       3897       3907       3917
AGATTTTGTT TTTATACTTG GAAGTGGTGA ATTATTTTAT ATAAAGTCAT TTAAATATCT ATTTAAAAGA 3927       3937       3947       3957       3967       3977
TAGGAAGCTG CTTATATATT TAATAATAAA AGAAGTGCAC AAGCTGCCGT TGACGTAGCT CGAG
```

PRODUCTION OF A RECOMBINANT HUMAN COLONY STIMULATING FACTOR

The present invention relates to a process for producing a recombinant protein, named CSF-69. More specifically, this invention relates to a method employing a novel DNA sequence and recombinant DNA molecule coding for a protein having the characteristics of a human CSF glycoprotein.

BACKGROUND

Colony stimulating factors (CSF) are a group of specific regulatory glycoproteins that stimulate hematopoietic cell proliferation and differentiation. They are also believed to affect the activity of subpopulations of mature hematopoietic cells which are important in a host defense against infection.

The study of hematopoiesis and the potential role of the hematopoietic cells in the immune response requires the ability to maintain and grow hematopoietic progenitor cells in vitro and in vivo. Thus CSFs may be employed as reagents for clinical testing and research study of the cells of the hematopoietic and possibly the immune systems. Several CSFs have been identified which may be useful for these purposes, e.g., CSFs that control granulocyte and macrophage populations, and CSFs that stimulate mast cells and stem cells. Several human granulocyte and/or macrophage CSFs have presently been identified [See D. Metcalf, "The Molecular Biology and Functions of the Granulocyte-Macrophage Colony Stimulating Factors," Blood, 67 (2): 257-267 (1986).]

A cDNA sequence for human urinary CSF-1 has been reported by E. S. Kawasaki, et al., Science, 230: 291-196 (1985), which when expressed in a COS cell transient expression system, produced a protein that competed with labeled murine CSF-1 in a radio-receptor assay. The protein also reportedly stimulated mouse bone marrow proliferation, resulting in predominantly monocytic lineage type colonies in the mouse bone marrow assay. The protein's biological activity was inhibited by neutralizing antisera for CSF-1.

These CSF glycoproteins have therapeutic potential in the treatment of diseases characterized by a decreased level of production of hematopoietic cells. In addition they may prove useful as activators of mature white cells in cases of serious infection. Leukopenia, a reduction in the number of circulating leucocytes (white cells) in the peripheral blood is a common affliction that may be induced by exposure to radiation or chemical carcinogens and exposure to certain viruses. It is often a side effect of various forms of cancer therapy. Therapeutic treatment of leukopenia with presently available drugs is ineffective and can result in undesirable side effects. There remains a need in the field for effective therapeutic agents for naturally occurring or radiation-induced leukopenia.

The ability to make large quantities of a protein exhibiting a high degree of human CSF activity will facilitate the study of the biological properties of the progenitor cells involved in the formation of all types of circulating blood cells. The availability of such proteins will also aid in evaluating the roles of other growth factors as well as provide potential therapeutic agents for treating leukopenias, generalized cytopenias and serious infections and potentially aid in regulating immune functions.

THE INVENTION

As one aspect of the present invention, there is provided a novel method for producing a protein exhibiting the colony stimulating characteristics of a human CSF. This protein may also be capable of stimulating accessory and mature cells, e.g. monocytes, to produce another CSF-like factor which itself causes the formation of colonies as well as other CSF-type activities. The method of the present invention involves culturing a suitable cell or cell line, such as COS-1, CV-1, Chinese hamster ovary cells (CHO) and the like, which has been transformed with a vector containing the cDNA sequence depicted in FIG. 2. The vector employed in the method also contains a suitable expression control sequence in operative association with the CSF-like DNA coding sequence.

Figure 1:
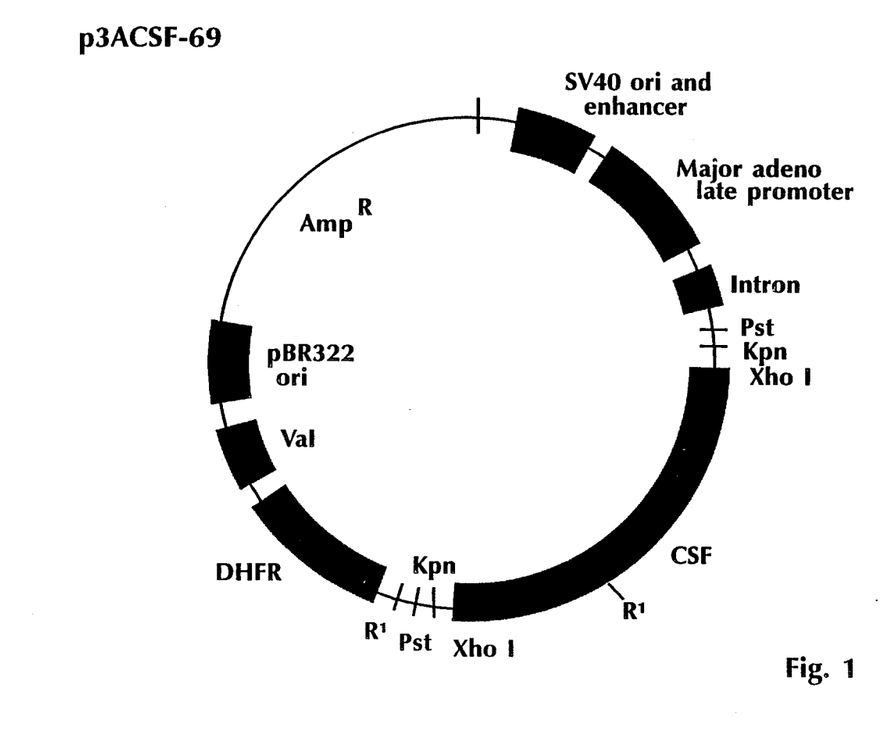
FIG. 1 is a schematic representation of plasmid p3ACSF-69.
Figure 2:
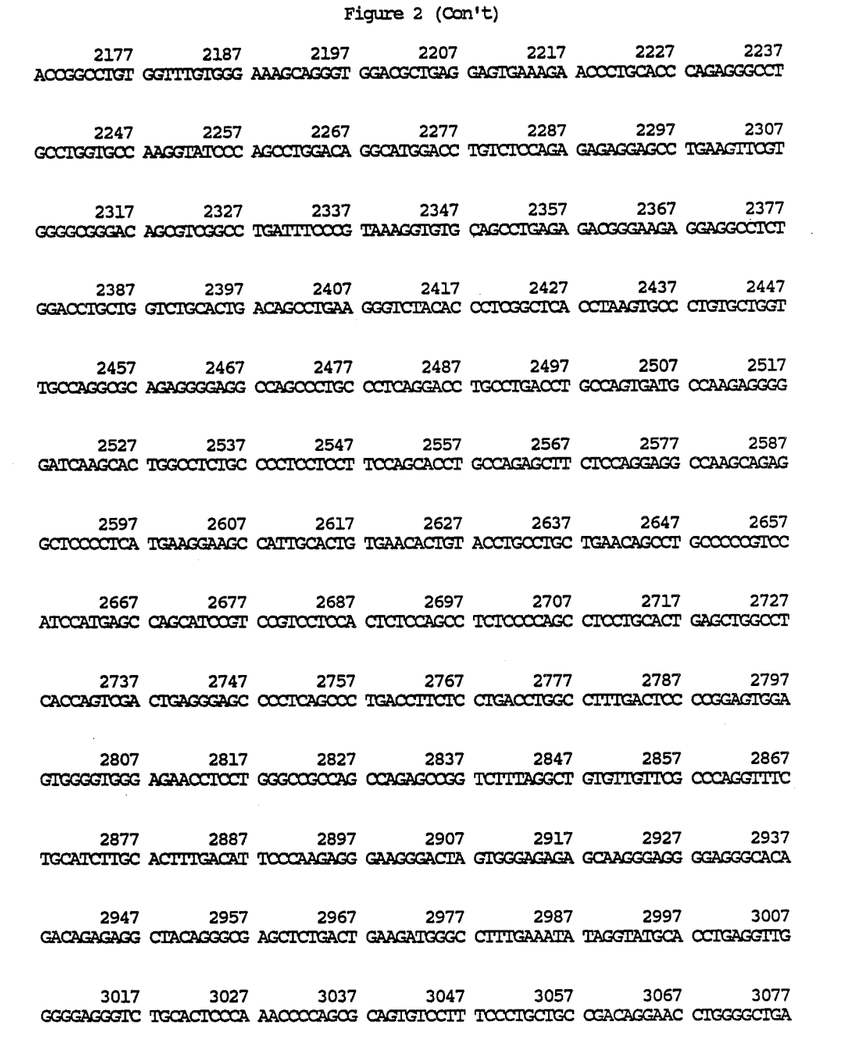
FIG. 2 shows the DNA sequence coding for CSF-69.

Another aspect of the present invention provides vectors for use in the method of expression of this CSF-like protein which contain the novel DNA sequence recited in FIG. 2. The 4 kb DNA sequence coding, on expression, for the novel CSF-like protein, named CSF-69, was isolated from poly A+ mRNA of the SV40 transformed trophoblast cell line TPA-30-1 [ATCC #CRL-1583]. This sequence, depicted in FIG. 2 below, contains three portions, i.e. from nucleotide #1 to #415, from nucleotide #419 to #689 and from nucleotide #1584 to #1823, which are identical to the Kawasaki, et al., supra, sequence. However, nucleotides #416 to #418 and #690 to #1583 represent sequences which do not disrupt the reading frame of the coding sequence. The protein coding region of the 4 kb sequence is believed to extend from nucleotide #146 (the adenine in the methionine) to nucleotide #1807 which is followed by a TAG stop codon. This region codes a 554 amino acid sequence illustrated in FIG. 2. The remaining sequences of the 4 kb region may have a regulatory role in transcription in the natural host.

This approximately 4 kb DNA sequence is harbored in plasmid p3ACSF-69 in E. coli HB 101, which has been deposited in the American Type Culture Collection, 12301 Parklawn Dr., Rockville, MD and given accession number ATCC 67092. The sequence codes on expression for the approximately 70 kd protein, CSF-69, which in p3ACSF-69 conditioned media demonstrates CSF-like activity in in vitro mouse and human bone marrow assays.

Slight variations in the 4 kb sequence of FIG. 2 which are caused by point mutations and the like should not change the functional protein for which the sequence codes on expression. Therefore, such minor variations in sequence are encompassed in the invention. Vectors incorporating these sequences are also embodiments of the present invention and useful in the production of CSF-like protein described herein.

A further aspect of the present invention is the novel protein itself, CSF-69. CSF-69 is characterized by an apparent molecular weight of approximately 70 kd when analyzed by polyacrylamide gel electrophoresis under non-reducing conditions. However, if this analysis is performed after reduction of the CSF-69, the protein is characterized by an apparent molecular weight of 35 kd suggesting that CSF-69 is a disulfide linked homodimer of 35 kd subunits.

As yet another aspect of the invention is a therapeutic composition for treating leukopenia and serious infection. Such a composition comprises a therapeutically effective amount of the CSF-69 protein in admixture with a pharmaceutically acceptable carrier. This composition can be systemically administered either parenterally, intravenously or subcutaneously. When systemically administered, the therapeutic composition for use in this invention is, of course, in the form of a pyrogen-free, parenterally acceptable aqueous solution. The preparation of such a parenterally acceptable protein solution, having due regard to pH, isotonicity, stability and the like, is within the skill of the art.

The dosage regimen will be determined by the attending physician considering various factors which modify the action of drugs, e.g. the condition, body weight, sex, and diet of the patient, the severity of any infection, time of administration and other clinical factors. Generally, the daily regimen should be in the range of 200–1000 micrograms of protein or 50 to 500 units of protein per kilogram of body weight. Progress can be monitored by periodic assessment of the hematological profile, e.g. white cell count and the like.

The following examples illustrate the method of the present invention employing the DNA sequence of FIG. 2 to produce CSF-69.

EXAMPLE I

Construction of an exemplary mammalian expression vector p3ACSF-69

To construct a mammalian vector for expression of the novel CSF-like protein, the cDNA sequence depicted in FIG. 2 above was adapted with restriction endonuclease enzyme XhoI linkers (New England Biolabs) and ligated into XhoI-digested, phosphatased COS cell expression vector pXMT2. pXMT2 contains the SV40 enhancer, major adenovirus late promoter, DHFR coding sequence, SV40 late message poly A addition site and VaI gene. pXMT2 further contains a linker sequence with restriction endonuclease sites for KpnI, PstI and XhoI. The plasmid resulting from the XhoI digestion of pXMT2 and the insertion of the linker and the XhoI adapted DNA sequence of FIG. 2 coding for a CSF-like protein was designated p3ACSF-69. p3ACSF-69 (ATCC #67092) can be transformed by conventional techniques into a suitable mammalian host cell for expression of the CSF-like protein. Exemplary host cells are mammalian cells and cell lines, particularly primate cell lines, rodent cell lines and the like.

One skilled in the art can also construct other mammalian expression vectors comparable to p3ACSF-69 by cutting the DNA sequence of FIG. 2 from the plasmid with XhoI and employing well-known recombinant genetic engineering techniques and other known vectors, such as pCD [Okayama et al., Mol. Cell Biol. 2: 161–170 (1982)] and pJL3, pJL4 [Gough et al., EMBO J., 4: 645–653 (1985)]. The transformation of these vectors into appropriate host cells can result in expression of the CSF-like protein.

Similarly, one skilled in the art could manipulate the sequence by eliminating or replacing the mammalian regulatory sequences flanking the coding sequence with yeast, bacterial or insect sequences to create non-mammalian vectors. Thus this sequence would then be expressable in yeast, bacterial or insect host cells. For example, the coding sequence of FIG. 2 could be cut from p3ACSF-69 with XhoI and further manipulated (e.g., ligated to other known likers or modified by deleting non-coding sequences therefrom or altering nucleotides therein by other known techniques). The modified CSF coding sequence could then be inserted into, for example, a known bacterial vector using procedures such as described in T. Taniguchi et al, Proc. Natl. Acad. Sci. U.S.A., 77: 5230–5233 (1980). This exemplary bacterial vector could then be transformed into bacterial host cells and the CSF-69 protein expressed thereby.

Similar manipulations can be performed for the construction of an insect vector [See, e.g., procedures described in published European patent application No. 155,476] or a yeast vector [See, e.g., procedures described in published PCT application WO No. 86 00639] for expression of the CSF protein in insect or yeast cells.

EXAMPLE II

Expression of a CSF-like Protein

Plasmid DNA, prepared from E. coli HB101 containing p3ACSF-69 as described in Maniatis et al., Molecular Cloning, A Laboratory Manual, Cold Spring Harbor Laboratory, (1982) was purified by conventional methods involving equilibrium centrifugation in cesium chloride gradients containing ethidium bromide. COS cells (ATCC CRL 1650) were transfected with the purified DNA at a concentration of approximately 5 ug plasmid DNA per $10^6$ COS cells and treated with chloroquine according to the procedures described in G. G. Wong et al., Science, 280: 810–815 (1985) and R. J. Kaufman et al. Mol. Cell Biol., 2: 1304 (1982). 72 hours following transfection p3ACSF-69 medium can be harvested containing a protein which demonstrates CSF-like activity in standard bone narrow assays, as discussed in Example III below.

EXAMPLE III

CSF Activity in In Vitro Assays

A. Mouse assay

Mouse bone marrow assays were conducted as described in D. Metcalf, The Hemopoietic Colony Stimulating Factors, Elsevier Press, New York (1984) with the following modifications.

(a) $2 \times 10^5$ bone marrow cells per ml were employed in the assay:
(b) final assay volume was 100 ul; and
(c) assays were set up in standard 96 well microtiter plates.

Bone marrow was obtained from the femurs of 6–25 week old female Balb/c mice (Jackson). Using WEHI 3 conditioned medium [J. C. Lee et al., J. Immunol., 128: 2393–2398 (1982)] which contains mouse interleukin-3 as a standard control, one dilution unit of activity was defined as that concentration of protein which results in a maximal response in this bone marrow assay, i.e., approximately 15 to 25 colonies per $2 \times 10^4$ mouse bone marrow cells.

p3ACSF-69 conditioned medium was found to be active to at least $10^{-4}$ dilution in a mouse bone marrow assay and produced mainly monocytic lineage type colonies. The number and type of cells in a maximal response will vary with the strain and age of the mouse donors.

B. Human Assay

Human bone marrow assays, employing non-adherent bone marrow cells, were performed as described in G. G. Wong, et al., supra. p3ACSF-69 conditioned medium was active to a 1:50 dilution in human bone marrow assays and produced predominantly monocytic lineage-type colonies.

EXAMPLE IV

Molecular Weight Analysis of the CSF-like Protein, CSF-69

Following the procedure of R. J. Kaufman and P. A. Sharp, *J. Mol. Biol.* 159: 601–629 (1982), $^{35}$S methionine can be metabolically incorporated into the CSF-69 protein made by COS cell transfection with p3ACSF-69 DNA. When $^{35}$S methionine labelled p3ACSF-69 conditioned medium is analyzed under non-reducing conditions by polyacrylamide gel electrophoresis, [U. K. Laemmli, Nature 227: 680–685 (1970)] a broad band, indicative of glycosylation, can be detected at an apparent molecular weight of approximately 70 kd. Corresponding transfection of pXMT2 vector DNA does not produce an equivalent $^{35}$S protein band.

$^{35}$S methionine labelled p3ACSF-69 conditioned medium was reduced with 100 mM beta-mercaptoethanol and analyzed by SDS polyacrylamide gel electrophoresis. The 70 kd band disappears and an approximately 35 kd, broad band, indicative of glycosylation, is detected. Reduced p3ACSF-69 conditioned medium is inactive in both mouse and human bone marrow assays. Thus the CSF-69 protein in p3ACSF-69 conditioned medium appears to be active as a dimer and inactive when it is reduced to its constitutive monomers.

$^{35}$S labelled, reduced p3ACSF-69 conditioned medium was treated with neuraminidase (Sigma) according to the procedures of M. Bradford, *Anal. Biochem* 72: 248 (1976) to remove sialic acid and with peptide N-glycosidase F [also known as N-glycanase (Genzyme)] to remove N-linked carbohydrates. Analysis by SDS polyacrylamide gel electrophoresis revealed an approximately 18 kd discrete band in the neuraminidase, N-glycosidase F treated p3ACSF-69 conditioned medium which was absent from the reduced untreated $^{35}$S methionine labelled p3ACSF-69 conditioned medium. Reduced $^{35}$S labelled p3ACSF-69 conditioned medium treated only with N-glycanase revealed an approximately 18 kd band in SDS-polyacrylamide gel electrophoretic analysis.

From N-glycosidase F and neuraminidase experiments, it appears that the novel CSF-69 protein produced by p3ACSF-69 is a dimer of two approximately 35 kd glycosylated monomers which each comprise an approximately 18 kd polypeptide that is extensively modified by N-linked glycosylation.

EXAMPLE V

Construction of CHO cell lines expressing high levels of CSF-69

One method for producing high levels of CSF-69 from mammalian cells involves the construction of cells containing multiple copies of the heterologous CSF-69 gene. The heterologous gene can be linked to an amplifiable marker, e.g., the dihydrofolate reductase (DHFR) gene for which cells containing increased gene copies can be selected for by propagation in increasing concentrations of methotrexate (MTX) according to the procedures of Kaufman & Sharp, *J. Mol. Biol.*, supra. This approach can be employed with a number of different cell types.

p3ACSF-69 contains the CSF-69 gene in operative association with other plasmid sequences enabling expression thereof. p3ACSF-69 and the DHFR expression plasmid pAdA26SV(A)3 (Kaufman & Sharp, Mol. Cell Biol., supra) can be co-introduced into DHFR-deficient CHO cells, DUKX-BII, by calcium phosphate coprecipitation and transfection. DHFR expressing transformants are selected for growth in alpha media with dialyzed fetal calf serum, and subsequently selected for amplification by growth in increasing concentrations of MTX (sequential steps in 0.02, 0,2, 1.0 and 5 μM MTX) as described in Kaufman, et al., *Mol. Cell Biol.* 5: 1750 (1983). Transformants are cloned, and biologically active CSF-69 protein expression is monitored by murine bone marrow assays. CSF-69 expression should increase with increasing levels of MTX resistance.

Numerous modifications and variations in practice of this invention are expected to occur to those skilled in the art upon consideration of the foregoing descriptions of preferred embodiments thereof. Such modifications and variations are believed to be encompassed in the appended claims.

What is claimed is:

1. A process for producing a protein capable of stimulating proliferation of monocytic cells in both human and mouse bone marrow assays comprising culturing host cells containing a DNA vector which contains a DNA sequence encoding the polypeptide sequence encompassing the mature form of the protein of FIG. 2, the DNA sequence being in operative association with an expression control sequence and recovering the protein so produced from the cultured host cells.

2. The process according to claim 1, wherein said cells are a mammalian cell line.

3. The process according to claim 2, wherein said cells are selected from the group consisting of a primate cell line, and a rodent cell line.

4. The process according to claim 1, wherein said vector is p3ACSF-69.

5. The process of claim 1, wherein the DNA is cDNA.

* * * * *

UNITED STATES PATENT AND TRADEMARK OFFICE
CERTIFICATE OF CORRECTION

PATENT NO.   : 4,879,227

DATED        : November 7, 1989

INVENTOR(S)  : Steven C. Clark, et al

It is certified that error appears in the above-identified patent and that said Letters Patent is hereby corrected as shown below:

The term of this patent subsequent to September 19, 2006, has been disclaimed.

Signed and Sealed this

Twenty-seventh Day of February, 1990

*Attest:*

JEFFREY M. SAMUELS

*Attesting Officer*          *Acting Commissioner of Patents and Trademarks*